United States Patent [19]
Jezzi et al.

[11] Patent Number: 5,558,655
[45] Date of Patent: Sep. 24, 1996

[54] ABSORBENT ARTICLE WITH DRY SURFACE COMPOSITE CONSTRUCTION

[75] Inventors: Arrigo D. Jezzi, Berwyn; Charles F. Schroer, Jr., Phoenixville; Caroline Gephart, Spring City; Daniel D. Biesterveld, Frazer, all of Pa.

[73] Assignee: Confab, Inc., King of Prussia, Pa.

[21] Appl. No.: 237,204

[22] Filed: May 3, 1994

[51] Int. Cl.$^6$ .............. A61F 13/15; A61F 13/20
[52] U.S. Cl. .......... 604/378; 604/372; 604/368; 604/385.1; 604/370
[58] Field of Search .................. 604/358, 365, 604/368, 372, 378, 379, 380, 385.1

[56] References Cited

U.S. PATENT DOCUMENTS

| | | | |
|---|---|---|---|
| 3,888,256 | 6/1975 | Studinger | 604/369 |
| 3,929,135 | 12/1975 | Thompson . | |
| 4,055,180 | 10/1977 | Karami | 604/378 |
| 4,055,184 | 10/1977 | Karami | 604/369 |
| 4,269,188 | 5/1981 | Nishizawa | 604/368 |
| 4,323,069 | 4/1982 | Ahr et al. | 604/372 |
| 4,324,246 | 4/1982 | Mullane et al. . | |
| 4,338,371 | 7/1982 | Dawn et al. | 604/368 |
| 4,342,314 | 8/1982 | Radel et al. . | |
| 4,381,783 | 5/1983 | Elias | 604/378 |
| 4,690,679 | 9/1987 | Mattingly, III et al. . | |
| 4,699,823 | 10/1987 | Kellenberger et al. . | |
| 4,798,603 | 1/1989 | Meyer | 604/378 |
| 4,806,411 | 2/1989 | Mattingly, III et al. . | |
| 4,842,794 | 6/1989 | Hovis et al. . | |
| 5,147,343 | 9/1992 | Kellenberger . | |
| 5,149,335 | 9/1992 | Kellenberger et al. . | |
| 5,188,624 | 2/1993 | Young, Sr. et al. | 604/358 |
| 5,411,497 | 5/1995 | Tanzer et al. | 604/368 |
| 5,425,725 | 6/1995 | Tanzer et al. | 604/368 |
| 5,433,715 | 7/1995 | Tanzer et al. | 604/368 |

*Primary Examiner*—David H. Willse
*Assistant Examiner*—P. Zuttarelli
*Attorney, Agent, or Firm*—Finnegan, Henderson, Farabow, Garrett & Dunner, L.L.P.

[57] ABSTRACT

An absorbent article, e.g. or a diaper, is disclosed which comprises a composite structure of a "two-dimensional" or very flat, apertured film or nonwoven layer, in combination with a fluid transferring layer and a superabsorbent polymer-containing laminate, and an absorbent core below the laminate to achieve superior dryness. The superabsorbent polymer-containing laminate, which contains airlaid fibrous components and superabsorbent polymers, swells to at least three times its dry caliper upon fluid introduction in order to achieve movement of the coverstock away from the absorbent core which permits the coverstock to remain relatively dry and avoids rewetting.

17 Claims, 2 Drawing Sheets

ABSORBENT ARTICLE WITH DRY SURFACE COMPOSITE CONSTRUCTION

BACKGROUND OF THE INVENTION

The present invention relates to an absorbent article. In particular, the present invention relates to an absorbent structure for disposition as a sanitary pad, incontinent pad, infant diaper, or similar fluid absorbing article that offers a marked degree of dryness over the surface of the insult area (i.e., soiled, for example, by liquid and/or solid voiding by the wearer).

Previous attempts for achieving dry surfaces and stain resistance to the surface of absorbent pads include a number of techniques disclosed hereinbelow. Mullane et al., U.S. Pat. No. 4,324,246, relates to a hydrophobic, liquid permeable topsheet having a caliper of less than 0.030 inches, an equivalent hydraulic diameter of less than 0.025 inches, and an open area of at least 35% to 55%. Radel et al., U.S. Pat. No. 4,342,314, relates to a resilient, liquid permeable, three-dimensional plastic material that forms a capillary network from laminated layers having corresponding apertures of decreasing cross-section which promote transmission of fluid through the structure without having lateral transmission of the fluid between adjacent capillary networks. In addition, Mattingly, III et al., U.S. Pat. No. 4,690,679, discusses an absorbent product which uses a coextruded apertured film having differing melting points which enhance fluid flow to the absorbent core and prohibits flow in the opposite direction (rewet). Mattingly, III et al., U.S. Pat. No. 4,806,411, further describes a coextruded apertured film having layers with differing melting points. The apertures have an equivalent circular diameter of 0.01 to 0.03 inches with a total open area of 20% to 70%. The thickness of the film is 1 to 10 mils.

Osborn, European Patent Application 0 336 578 A1, describes a thin, flexible sanitary napkin that utilizes an apertured formed film coversheet, an apertured nonwoven, wipe acquisition sheet, and an absorbent core containing 5–35% by weight of a particulate hydrogel-forming polymer gelling agent.

Meyer et al., U.S. Pat. No. 4,798,603, describes an absorbent structure having a hydrophobic, liquid permeable topsheet, a moisture impermeable bottom sheet, an absorbent core, and a liquid permeable transport layer between the topsheet and absorbent core which is less hydrophilic than the absorbent core and has an effective pore size which is smaller than the pore size of the topsheet layer.

Kellenberger et al., U.S. Pat. No. 4,699,823, relates to an article with an absorbent layer having a superabsorbent polymer contained therein. The absorbent layer further has a z-directional superabsorbent concentration gradient. Kellenberger, U.S. Pat. No. 5,147,343, describes diapers and other specific absorbent articles having a porous fiber matrix with superabsorbent material present in the matrix so that the superabsorbent material can absorb a given amount of fluid while under a certain applied pressure. Kellenberger et al., U.S. Pat. No. 5,149,335, describes an absorbent structure which utilizes a superabsorbent material contained within a fibrous matrix or between layers of the fibrous material, having a free swell rate of less than about 60 seconds, a five minute absorbency under loads of at least 15 grams of fluid per gram of absorbent, and an amount of superabsorbent material which is 60 to 100 weight percent based on the total weight of the containment means (e.g. absorbent plus superabsorbent).

Current products which offer the feature of a marked degree of dryness over the surface of the insult area after the absorbent pad has been insulted utilize a "three dimensional" apertured film (e.g., a film that has conical or similar formed apertures) to achieve dryness. This type of plastic film typically is treated with surfactants to reduce hydrophobicity.

It is an object of the present invention to provide an absorbent article which utilizes a composite structure of a "two dimensional" or very flat, apertured film or a non-woven layer, in combination with a layer of fluid transferring material, a superabsorbent polymer-containing laminate below the fluid transferring material and an absorbent core below the laminate to achieve dryness.

Additional objects and advantages of the present invention will be set forth in part in the description which follows, and in part will be apparent from the description, or may be learned by practice of the present invention. The objects and advantages of the present invention will be realized and attained by means of the elements and combinations particularly pointed out in the appended claims.

SUMMARY OF THE INVENTION

To achieve the objects and in accordance with the purpose of the present invention, as embodied and broadly described herein, the present invention comprises an absorbent article having a multi-layered coverstock wherein the top layer is a two dimensional apertured film or nonwoven layer and the bottom layer is a fluid transferring material. Beneath the coverstock are a superabsorbent polymer-containing laminate, an absorbent core, and a liquid impermeable backsheet. The superabsorbent polymer-containing laminate and absorbent core are situated between the coverstock and liquid impermeable backsheet. Also, the superabsorbent polymer-containing laminate swells to at least three times its dry caliper upon wetting, which lifts or moves the coverstock away from the wet surface of the absorbent core.

It is to be understood that both the foregoing general description and the following detailed description are exemplary and explanatory only and are not restrictive of the present invention as claimed.

DETAILED DESCRIPTION OF THE PRESENT INVENTION

Figure 1:
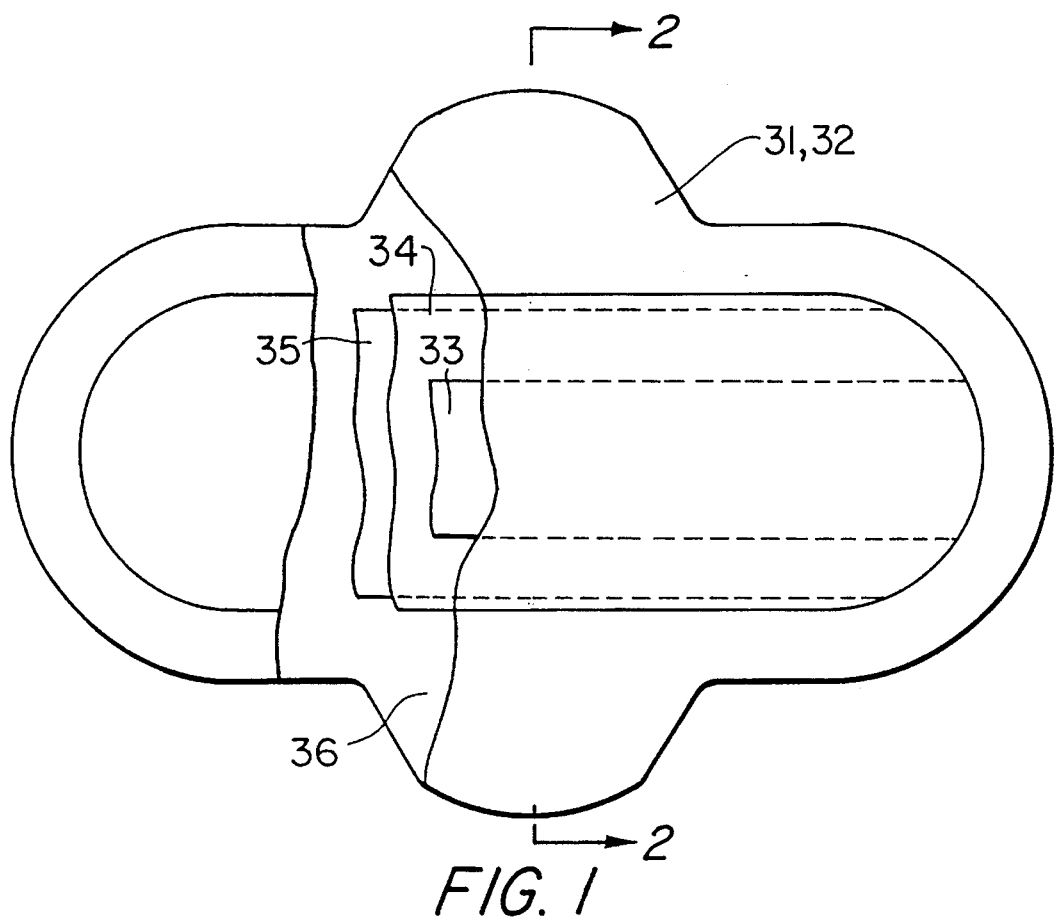
FIG. 1 is a top plan view of a sanitary napkin embodiment of the present invention having portions cut away to reveal its underlying structure.
Figure 2:
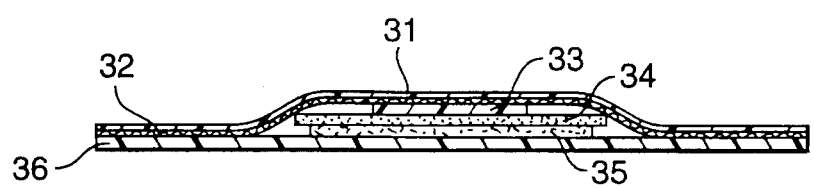
FIG. 2 is a cross-sectional view taken along section line 2—2 of FIG. 1.
Figure 3:
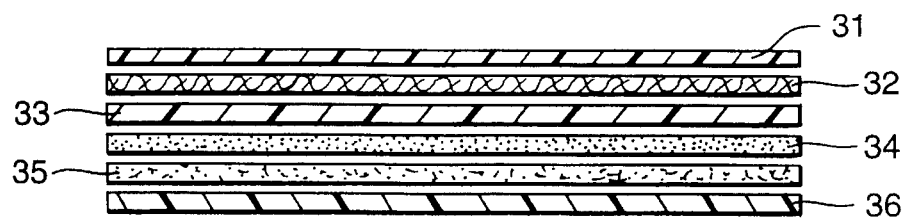
FIG. 3 is an enlarged cross-sectional view of a preferred absorbent article.

Referring to FIGS. 1–3, one preferred embodiment of the absorbent article of the present invention includes a hydrophobic layer (31) made of a two dimensional apertured film or a net-like fabric (e.g., nonwoven), not shown, such as described by Hovis et al., U.S. Pat. No. 4,842,794, incorporated herein by reference in its entirety, or other layer of similar construction. Underneath hydrophobic layer (31) is a layer (32) of high loft, thermally bonded nonwoven or similar fluid transferring material that in combination with hydrophobic layer (31), comprises the multi-layered coverstock, and provides for a fluid permeable covering with sufficient loft. Generally, a sufficiently high loft refers to a thickness or caliper of at least 0.25 mm or greater. Beneath or under the two layered coverstock (31, 32) is a superabsorbent polymer-containing laminate (33). The laminate (33) is located between the coverstock (31, 32) and an absorbent core (34, 35) which is preferably a layer (34) of airlaid fibrous material treated with a latex binder such as latex treated pulp, and preferably a layer (35) of pulp fluff situated below the airlaid material. Situated below the absorbent core (34, 35) is a liquid impermeable backsheet (36). The first layer of the absorbent core and the superabsorbent polymer-containing laminate (33) provide a means for retaining a portion of the introduced fluid which activates the superabsorbent polymer in the laminate causing swelling. This swelling of the laminate (33) provides a means for lifting or moving the coverstock (31, 32) away from the wet surface of the absorbent core (34, 35). This lifting or moving action provides a means for preventing rewet (i.e., preventing the fluid introduced to the absorbent article via the coverstock (31, 32) from returning to the surface of the article or pad), thereby enhancing the performance of the absorbent article by providing a relatively dry surface to the user over the insulted area.

The absorbent article (e.g, a sanitary napkin, diaper, or incontinent article), is manufactured so that the superabsorbent polymer-containing laminate is positioned above or on top of the absorbent core. The laminate and core are encased between the coverstock and backsheet by any art recognized technique. In one preferred embodiment, the multi-layered coverstock and the liquid impermeable backsheet preferably extend around their entire perimeter beyond the edges of the absorbent core and laminate. These layers are preferably joined together at that portion extending beyond the absorbent core and laminate to encase the core and laminate therein. More preferably, a continuous band of hot melt adhesive is applied around the entire perimeter of the portions of the coverstock and backsheet which extend beyond the absorbent core such that they are sealed together. Other suitable means known in the art such as ultrasonic sealing or heat/pressure sealing or crimping in any suitable configuration such as lines or closely spaced intermittent dots and dashes can alternatively be used. The sealing of the edges of the coverstock to the edges of the liquid impermeable backsheet encases all of the remaining components between the coverstock and backsheet to form the absorbent article.

The two layered coverstock is preferably a two dimensional apertured plastic film outer layer and a thermally bonded nonwoven inner layer.

The term "two dimensional," as used herein, indicates that the apertured film is considered relatively flat as compared to three dimensional apertured films which have conical structures similar to those set forth in Thompson, U.S. Pat. No. 3,929,135. Instead of apertured film, a nonwoven can be used as long as the nonwoven provides the same desired properties. Generally, the nonwoven will have similar caliper as the two dimensional apertured film of the present invention.

The preferred two dimensional apertured plastic film outer layer is two dimensional and manufactured having an embossed caliper of less than 0.020 inch, a total open area of about 35% or less, and an equivalent hydraulic diameter greater than 0.025 inch but less than 0.050 inch. A suitable apertured plastic film is manufactured by Applied Extrusion Technologies and is marketed as Delnet CKX-215, texturized. To further reduce the plastic feel of the apertured plastic film outer layer, the top surface facing the body can be embossed which will also lower the gloss appearance of the top surface thereof. Such embossing techniques are known in the art and include that of Hovis et al., discussed above.

The preferred thermally bonded nonwoven inner layer has a basis weight of less than 40 grams per square meter but greater than 20 grams per square meter, an embossed caliper of less than 0.020 inch, and an embossed surface area of less than 25%. The total caliper of the two layered coverstock is preferably greater than 0.030 inch. A suitable thermally bonded nonwoven cover layer is manufactured by Fibertech Group, Inc. and marketed in the trade as Thermally Bonded Polypropylene Intermediate, 30 gsm.

Optionally, a hydrophobic coating or surface treatment with a hydrophobic solution can be placed on the top surface of the thermally bonded nonwoven layer. This hydrophobic coating should be fluid permeable. Further, this hydrophobic coating provides a raised surface off of the thermally bonded nonwoven layer to inhibit fluids from rewetting the top surface thereof. Preferably, the thickness of the coating should be from about 0.0002 mm to about 0.0762 mm. The use of a hydrophobic coating on the thermally bonded nonwoven layer would also prevent fluid introduced to the absorbent article via the coverstock from returning to the top surface of the absorbent article which would thereby enhance the performance of the absorbent article by providing a relatively dry surface over the insulted area. Typical examples of hydrophobic coatings are known to those skilled in the art and include a fluorocarbon treatment.

While not necessary, the outer and inner layers of the coverstock can be bonded together by adhesive means, e.g. hot melt, or by other suitable means known in the art such as ultrasonic bonding or heat/pressure sealing. A preferred commercially available hot melt is Findley H-1251-01.

One preferred superabsorbent polymer-containing laminate is manufactured using a super absorbent polymer which has a high absorbency under load characteristic, such as, but not limited to, Hoechst-Celanese Sanwet IM-3900, at a loading of not less than 50 grams per square meter, which has an absorbency under load minimum of 26 grams of fluid per gram of superabsorbent polymer.

In one preferred embodiment, to form the laminate, the super absorbent polymer is sandwiched between a top and bottom layer of not more than a 70 pound per ream airlaid material. The airlaid material can be comminuted wood pulp fibers in combination with a latex binder. The caliper of the superabsorbent polymer laminate is preferably less than 0.050 inch. The superabsorbent polymer-containing laminate containing the airlaid components and the superabsorbent polymer should swell to at least three times its dry caliper upon fluid introduction in order to achieve a preferred degree of lifting or moving of the coverstock away from the absorbent core. The polymer-containing laminate can be positioned in any manner which upon fluid contact achieves the lifting or moving of the coverstock to prevent rewet. Preferably, the superabsorbent polymer-containing laminate is centrally and longitudinally positioned on the absorbent core, going completely to the ends of the absorbent core but preferably covering no less than about 30% of the width of the core. The laminate may be a free floating layer but is preferably attached to the top or upper surface of the absorbent core. Any attachment means can be used, e.g. adhesive means. In addition, the top or upper surface of the superabsorbent polymer-containing laminate can be bonded to the surface of the thermally bonded nonwoven layer facing the superabsorbent polymer-containing laminate. This bonding can achieve more intimate contact between the two surfaces and can enhance the fluid transfer between these layers. The bonding of the two layers can be accomplished by the same attachment means described above.

Though not necessary, more than one superabsorbent polymer-containing laminate can be used and it is within the scope of the present invention to use parallel layers of superabsorbent polymer-containing laminates depending upon the intended use of the absorbent article of the present invention.

One preferred absorbent core is manufactured with an upper layer of not more than a 70 pound per ream airlaid material, which preferably is comminuted wood pulp fibers bound or held together with the addition of a latex binder, and a lower layer of densified wood pulp fluff, having a basis weight of not more than 400 grams per square meter. The airlaid materials utilized in both the superabsorbent polymer-containing laminate and in the upper layer of the absorbent core (above the fluff of the absorbent core) are preferably bound or held together with a latex type binder, such as a polyvinyl acetate copolymer, or an ethylene vinyl acetate copolymer. The binder should be used in an amount of at least 25 percent total solids in order to properly coat the airlaid fibers so that fluid is transferred through the fibers rather than absorbed. The main area of absorption is the fluff core (lower layer of the absorbent core) which preferably hold at least 60 percent of the fluid introduced into the absorbent article.

Other embodiments of the absorbent core can alternatively be used. For example, the absorbent core can be a single or multilayer structure comprising wood pulp fluff alone or airlaid material modified with a latex type binder alone. Also, the absorbent core can be constructed such that the upper layer is wood pulp fluff and the lower layer is airlaid material modified with a latex binder.

The backsheet is impervious to liquids and is preferably manufactured from a thin flexible film, although other flexible liquid impervious materials may also be used. The backsheet prevents the exudates absorbed and contained in the absorbent core from wetting articles which contact the diaper such as bed sheets and undergarments. Preferably, the backsheet is a polyethylene film having a thickness of from about 0.0012 mm (0.5 mil) to about 0.051 mm (2.0 mils), although other flexible liquid impervious materials may be used. As used herein, the term "flexible" refers to materials which are compliant and which will readily conform to the general shape and contours of the human body.

A suitable polyethylene film is manufactured by Filmtech and marketed in the trade as FT-355 Pink. The backsheet is preferably embossed and/or matte finished to provide a more clothlike appearance. Further, the backsheet may be perforated or otherwise modified to permit vapors to escape from the absorbent core while still preventing exudates from passing through the backsheet.

The size of the backsheet is dictated by the size of the wearer and the exact absorbent article design selected. In a preferred embodiment, the backsheet (36) has a modified elliptical shape (as shown in FIG. 1) extending beyond the edges of the absorbent core (34, 35) a minimum distance of at least about 1.3 cm to about 2.5 cm (about 0.5 to 1.0 inch) around the entire product perimeter. In the case where the absorbent article is a sanitary napkin, the moisture barrier or liquid impermeable backsheet preferably has a suitable garment attachment adhesive coated to the outside surface (facing the garment of the wearer). Such garment attachments are known in the art and include velcro-type fasteners, pressure sensitive adhesive types or hot melt pressure sensitive adhesives.

The overall caliper of a preferred construction for sanitary products is less than 6.5 millimeters, although thicker embodiments are possible. Other embodiments include diapers, both infant and adult, and other incontinent products.

With regard to the shape of the overall absorbent article, any shape is within the bounds of the present invention including dumbbell, hourglass, and rectangular. In order to obtain the desired shape of the absorbent article, the coverstock, backsheet, and the absorbent core should essentially have the desired shape.

The present invention will be further clarified by the following examples, which are intended to be purely exemplary of the invention.

EXAMPLES

Various experiments were performed in the development of the construction of the preferred embodiment. The test used in evaluating these constructions required that 10 milliliters of a 1.0%, dyed saline solution be introduced to the test article's surface through a one inch diameter, cylindrical opening, under a load of about 0.06 PSI, until the fluid in the cylindrical opening achieved strike through.

Strike through was measured as the time in seconds from when the insult fluid made contact with the article's surface until the fluid passed through the surface of the article. The load was removed from the pad and after two minutes the fluid stain was measured.

Stain is not evaluated as a surface characteristic but as a visual perception of what the user would see on the used product. The stain was measured at the widest portion of the stained area, in millimeters.

The rewet characteristic was measured five minutes after fluid introduction by applying a stack of absorbent filter papers, such as VWR Grade#417, over the insult surface, under a load of about 0.5 PSI, for fifteen seconds, then weighing the filter papers to measure any fluid which may have transferred from the pad to the filter paper. The objective of this type of evaluation was to assess the rewet characteristics of various constructions in order to understand which constructions were able to achieve low rewet values. Rewet is defined as the amount of insult fluid which transfers back through the coverstock after the pad has been insulted and a load has been applied. Ideally, a "zero" rewet is the best performance possible. Any fluid which is retained on the surface of an absorbent article, such as a sanitary napkin is undesirable since it tends to cause discomfort to the user.

Examples of a three dimensional apertured film, apertured film constructions which did not perform to acceptable levels, and examples of the preferred embodiments are set forth in Table 1.

The following components were used in the examples:

Walkisoft FG407 airlaid material in the absorbent core

Superabsorbent polymer-containing Laminate—using above airlaid and Chemdal Stockhausen 800 (superabsorbent polymer)

Superabsorbent polymer-containing Tissue used in Example 9: Lantor L412

Delnet CKX-215 texturized (2-Dimensional film) ITT Rayonier XJ HME pulp

Filmtech FT355 1.1 mil polyethylene film (backsheet)

Fibertech Intermediate 30 gsm thermally bonded polypropylene (fluid transferring material-thermally bonded nonwoven material)

Three dimensional film used in Example 1: Guialveole (3-D film) from Guial S. A.

Spun bound nonwoven used in Example 13: Fiberweb 0.55 MLP-V09U Spunbonded polypropylene Tissue used in Example 11: Cellutissue 2005 1216/ream tissue

TABLE 1

| Example No. | Construction | Strike Through | Rewet | Stain |
|---|---|---|---|---|
| 1 | Three dimensional film/ airlaid material (60 lb/ream)/ superabsorbent laminate/ wood pulp fluff (270 g/sq. m)/moisture barrier | 1.83 s | 0.00 g (comparative) | 53 mm |
| 2 | Two dimensional film/ superabsorbent laminate/ airlaid material (60 lb/ream)/wood pulp fluff (270 g/sq. m)/ moisture barrier | 1.75 s | 0.10 g (comparative) | 65 mm |
| 3* | Two dimensional film/ thermally bonded nonwoven/superabsorbent laminate strip/airlaid material (60 lb/ream)/ wood pulp fluff (270 g sq. m)/moisture barrier | 1.98 s | 0.02 g (present invention) (*preferred embodiment) | 65 mm |
| 4 | Two dimensional film/ thermally bonded nonwoven/airlaid material (60 lb/ream)/ wood pulp fluff (270 g/sq. m)/moisture barrier | 1.64 s | 1.49 g (comparative) | 75 mm |
| 5 | Two dimensional film/ thermally bonded nonwoven/superabsorbent laminate strip/wood pulp fluff (270 g/sq. m)/ moisture barrier | 2.30 s | 0.01 g (present invention) | 73 mm |
| 6 | Two dimensional film/ thermally bonded nonwoven/two parallel strips of superabsorbent laminate/airlaid material (60 lb/ream)/wood pulp fluff (270 g/sq. m)/ moisture barrier | 3.45 s | 0.02 g (present invention) | 95 mm |
| 7 | Two dimensional film/ thermally bonded nonwoven/sprinkled superabsorbent in fluff/ airlaid material (60 lb/ream)/wood pulp fluff (270 g/sq. m)/ moisture barrier | 1.78 s | 0.07 g (comparative) | 80 mm |
| 8 | Two dimensional film/ thermally bonded nonwoven/airlaid material (60 lb/ream)/ superabsorbent laminate strip/wood pulp fluff (270 g/sq. m)/moisture barrier | 2.57 s | 0.20 g (comparative) | 90 mm |
| 9 | Two dimensional film/ thermally bonded nonwoven/airlaid material (60 lb/ream)/ superabsorbent tissue strip/wood pulp fluff | 6.60 s | 0.37 g (comparative) | 90 mm |

TABLE 1-continued

| Example No. | Construction | Strike Through | Rewet | Stain |
|---|---|---|---|---|
| | (270 g/sq. m)/moisture barrier | | | |
| 10 | Two dimensional film/ thermally bonded nonwoven/c-folded airlaid material (60 lb/ream)/super-absorbent laminate strip/wood pulp fluff (200 g/sq. m)/moisture barrier | 3.08 s | 0.02 g (present invention) | 100 mm |
| 11 | Two dimensional film/ thermally bonded nonwoven/tissue (12 lb/ream)/ superabsorbent laminate strip/wood pulp fluff (270 g/sq. m)/moisture barrier | 1.56 s | 0.28 g (comparative) | 42 mm |
| 12 | Two dimensional film/ thermally bonded nonwoven/superabsorbent laminate strip/wood pulp fluff (270 g/sq. m)/ airlaid material (37 lb/ream)/moisture barrier | 1.83 s | 0.03 g (present invention) | 45 mm |
| 13 | Spunbond nonwoven/ airlaid material (60 lb/ream)/super-absorbent laminate strip/woodpulp fluff (200 g/in$^2$)/moisture barrier | 2.05 s | 0.05 g (present invention) | 53 mm |

The superabsorbent polymer-containing laminate, positioned on the top surface of the absorbent core and in combination with the preferred coverstock as described, leads to the overall excellent performance of the present invention.

A method for evaluating the dryness of the superabsorbent polymer-containing laminate alone was developed which correlates directly to the test results for the full absorbent construction.

Figure 4:
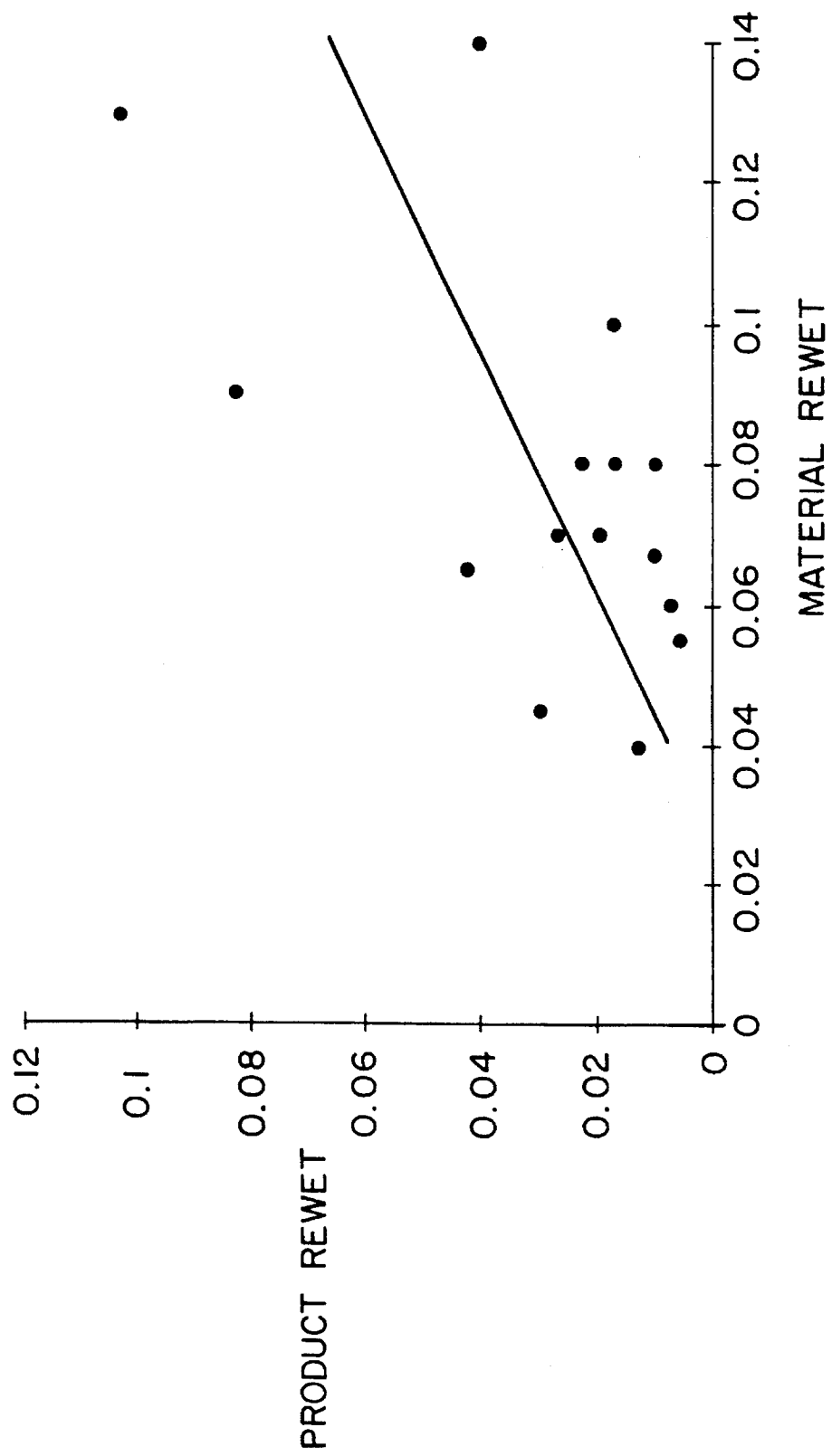
FIG. 4 is a graph comparing product rewet properties with material rewet properties.

A superabsorbent polymer-containing laminate sample of the dimensions described in the preferred embodiment was insulted with 5 milliliters of 1.0% saline solution in the same manner as described in the previously defined absorbency, rewet, and stain test for the full construction. The rewet of the laminate was measured under a load of about 1.0 PSI and was measured as described previously defined in the rewet test for the full construction. It is important to note that the rewet characteristic of the laminate has a direct effect on the degree of rewet in the full construction. FIG. 4 provides a comparison of test data showing this correlation. Rewet values of less than 0.10 grams are preferred for obtaining low rewets on the full construction. The superabsorbent polymer-containing laminate should swell at least three times its dry caliper, as indicated in the preferred embodiment, in order to raise or move the coverstock away from the absorbent core. This can be measured by determining the percent difference of dry caliper versus wet caliper, after the rewet test has been performed.

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An absorbent article which minimizes rewet comprising:
    a multi-layered coverstock having top and bottom layers, wherein the top layer is a two dimensional apertured film having a total open area of 35% or less and the bottom layer is a fluid transferring material;
    a superabsorbent polymer-containing laminate which swells to at least three time its dry caliper upon wetting situated below said fluid transferring material;
    an absorbent core below said laminate; and
    a liquid impermeable backsheet below said absorbent core, wherein said superabsorbent polymer-containing laminate and absorbent core are situated between said coverstock and liquid impermeable backsheet
wherein said superabsorbent polymer-containing laminate moves at least a portion of said coverstock away from said absorbent core to substantially prevent fewer of said coverstock by fluid contained within said core.

2. The absorbent article of claim 1, wherein said coverstock is hydrophobic.

3. The absorbent article of claim 1, wherein said fluid transferring material is a thermally bonded nonwoven material.

4. The absorbent article of claim 3, wherein said fluid transferring material has a high loft.

5. The absorbent article of claim 1, wherein said superabsorbent polymer-containing laminate comprises a superabsorbent polymer sandwiched between layers of airlaid fibrous material.

6. The absorbent article of claim 1, wherein said absorbent core comprises an upper layer and a lower layer of fibrous material.

7. The absorbent article of claim 6, wherein said fibrous material in at least one of said layers is modified with a latex binder.

8. The absorbent article of claim 7, wherein said latex binder is selected from the group consisting of a polyvinyl acetate copolymer and an ethylenevinyl acetate copolymer.

9. The absorbent article of claim 1, wherein said apertured film has an embossed caliper of less than about 0.020 inch.

10. The absorbent article of claim 1, wherein said apertured film has an equivalent hydraulic diameter greater than 0.025 inch but less than 0.050 inch.

11. The absorbent article of claim 3, wherein said thermally bonded nonwoven material has a basis weight of less than 40 grams per square meter.

12. The absorbent article of claim 3, wherein said thermally bonded nonwoven material has an embossed caliper of less than 0.020 inch.

13. The absorbent article of claim 3, wherein said thermally bonded nonwoven material has an embossed surface area of less than 25%.

14. The absorbent article of claim 1, wherein the total caliper of the multi-layered coverstock is greater than 0.030 inch.

15. The absorbent article of claim 1, wherein said absorbent article is a sanitary napkin.

16. The absorbent article of claim 1, wherein said absorbent article is a diaper.

17. The absorbent article of claim 16, wherein said absorbent article is an incontinent pad.

* * * * *

UNITED STATES PATENT AND TRADEMARK OFFICE
CERTIFICATE OF CORRECTION

PATENT NO. : 5,558,655
DATED : September 24, 1996
INVENTOR(S) : Arrigo D. JEZZI et al.

It is certified that error appears in the above-indentified patent and that said Letters Patent is hereby corrected as shown below:

Claim 1, column 9, line 19, "fewer" should read --rewet--.

Signed and Sealed this

Twenty-sixth Day of November 1996

Attest:

BRUCE LEHMAN

*Attesting Officer*  *Commissioner of Patents and Trademarks*